United States Patent [19]

Bradfute et al.

[11] Patent Number: 5,475,029
[45] Date of Patent: Dec. 12, 1995

[54] FARNESYL COMPOUNDS AS CHOLESTEROL LOWERING AGENTS

[75] Inventors: David L. Bradfute, Wooster, Ohio; Robert D. Simoni, Palo Alto, Calif.

[73] Assignee: The Board of Trustees of the Leland Stanford Junior University, Stanford, Calif.

[21] Appl. No.: 88,698

[22] Filed: Jul. 8, 1993

[51] Int. Cl.$^6$ .......................... A61K 31/23; A61K 31/08; A61K 31/045

[52] U.S. Cl. .......................... 514/549; 514/722; 514/739; 560/205; 568/687

[58] Field of Search .................................. 514/549, 739, 514/722; 560/205; 568/687

[56] References Cited

U.S. PATENT DOCUMENTS

| | | | |
|---|---|---|---|
| Re. 33,885 | 4/1992 | Mattson | 514/53 |
| 4,434,179 | 2/1984 | Kobayashi et al. | 424/308 |
| 4,871,720 | 10/1989 | Jaeggi | 514/79 |
| 5,025,003 | 6/1991 | Biller | 514/120 |
| 5,026,554 | 6/1991 | Bartizal et al. | 424/404 |

FOREIGN PATENT DOCUMENTS

| | | |
|---|---|---|
| 0696740 | 10/1964 | Canada . |
| 0356866 | 8/1989 | European Pat. Off. . |
| 0031614 | 2/1982 | Japan . |

OTHER PUBLICATIONS

CA 106:196638, Toshihiro et al, Isoprenyl Benzoates (1985).

Datey et al, "Ethyl Linoleate as an Antiatherogenic Agent", Angiology, Oct. 1966, 17(10) pp. 732–737.

Spady et al, "Regulation of Plasma LDL-Cholesterol Levels by Dietary Cholesterol and Fatty Acids", Annul. Rev. Nutr., 1993, 13:355–381.

Biller et al., "Isoprenoid (Phosphinylmethyl)phosphonates as Inhibitors of Squalene Synthetase", *Journal of Medicinal Chemistry*, 31(10):1869–1871 (1988).

Parker et al., "Tocotrienols Regulate Cholesterol Production in Mammalian Cells by Posttranscriptional Suppression of 3–Hydroxy–3–methylglutaryl–Coenzyme A Reductase", *The Jounal of Biological Chemistry*, 268(15):11230–11238 (1993).

Pearce et al., "Hypocholesterolemic Activity of Synthetic and Natural Tocotrienols", *J. Med. Chem.*, 35:3595–3606 (1992).

Sugiyama et al., "Isolation of Plasma Cholesterol–Lowering Components from Ningyotake (*Polyporus confluens*) Mushroom", *J. Nutr. Sci. Vitaminol.*, 38:335–342 (1992).

*Primary Examiner*—Allen J. Robinson
*Assistant Examiner*—Deborah Lambkin
*Attorney, Agent, or Firm*—Bertram I. Rowland; Pamela J. Sherwood

[57] ABSTRACT

Farnesyl derivatives, particularly farnesyl acetate, are used to lower the 3-hydroxy-3-methylglutaryl coenzyme A (HMG-CoA) reductase activity in cells, thereby reducing cholesterol biosynthesis. The compounds may be administered to hypercholesterolemia patients to reduce the overall level of serum cholesterol, either alone or in conjunction with other drugs conventionally used for the treatment of hypercholesterolemia.

4 Claims, No Drawings

FARNESYL COMPOUNDS AS CHOLESTEROL LOWERING AGENTS

This invention was made with Government support under contract 5R01HL26502. The Government has certain rights in this invention.

INTRODUCTION

1. Technical Field

The field of this invention is the treatment of hypercholesterolemia with pharmaceutically active compounds that reduce cholesterol synthesis.

2. Background

Atherosclerotic cardiovascular disease is a major cause of death in the United States. Atherosclerosis has a complex etiology, resulting from interactions between multiple genes and environmental factors. Among the risk factors is high blood cholesterol. The level of blood cholesterol is affected by the patient's diet, the proteins which carry lipids in the bloodstream, and the enzymes involved in cholesterol biosynthesis.

The biosynthetic pathway which leads to cholesterol synthesis is tightly regulated in normal cells. From the starting product 3-hydroxy-3-methylglutaryl coenzyme A (HMG CoA), the pathway produces metabolic products which include sterols and isoprenoid products which are essential for cell function. The primary rate limiting enzyme in the pathway is HMG CoA reductase. Its activity is regulated at the level of transcription, translation, degradation and a switch from inactive to an active form. Regulation can occur by both sterol and non-sterol products of the pathway.

Inhibition of HMG CoA reductase activity results in a decrease in total serum cholesterol and LDL cholesterol levels. Currently, the most widely prescribed drugs for hypercholesterolemia are competitive inhibitors of HMG CoA reductase. While these drugs are highly effective at lowering the rate of cholesterol synthesis, they may also enhance production of HMG CoA reductase, resulting in an increase in the amount of HMG CoA reductase over normal levels, thereby potentially mitigating their cholesterol lowering effect. It would be desirable to have a drug which decreases the level of serum cholesterol without increasing the level of HMG CoA reductase.

RELEVANT LITERATURE

U.S. Pat. No. 5,026,554 describes the squalene synthase inhibitor zaragozic acid. Billet, et al (1988) Journal of Medicinal Chemistry 31:1869 describes isoprenoid phosphinates that function as squalene synthase inhibitors in vitro, but are not effective in vivo. U.S. Pat. No. 4,871,720 describes pyrophosphinates used in the treatment of bone disorders, which function as squalene synthase inhibitors.

K. Sugiyama, et al (1992) J. Nutr. Sci. Vitamin. 38:335–342 evaluates the aromatic farnesyl derivatives grifolin and neogrifolin as cholesterol lowering agents.

U.S. Pat. No. 5,025,003 describes a number of isoprenoid derivatives stated to be useful for inhibiting cholesterol biosynthesis. The compounds found to be effective require a phosphate moiety and a salt of a carboxylic acid. European patent No. 356,866 describes the use of farnesyloxyphosphonylmethylphosphonates and analogs thereof as inhibitors of squalene synthetase.

SUMMARY OF THE INVENTION

Methods are provided to reduce levels of cholesterol in mammalian cells. The primary rate-limiting enzyme in cholesterol biosynthesis, 3-hydroxy-3-methylglutaryl coenzyme A (HMG CoA) reductase, is down-regulated by the presence of farnesyl compounds of the formula:

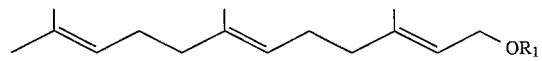

where $R_1$ may be a lower alkyl, or an acyl group

where $R_2$ may be any lower alkyl. The farnesyl compounds lower the steady state level of HMG CoA reductase, thereby reducing cholesterol biosynthesis. The compounds find use in the treatment of hypercholesterolemia, by reducing the level of serum cholesterol.

DESCRIPTION OF THE SPECIFIC EMBODIMENTS

Methods are provided to reduce the biosynthesis of cholesterol in cells. Farnesyl ester and ether compounds lower 3-hydroxy-3-methylglutaryl coenzyme A (HMG CoA) reductase activity in cells, thereby lowering cholesterol levels. The compounds may be administered to patients to reduce their serum cholesterol levels.

Novel methods are provided which employ compounds that are effective in decreasing the level of HMG CoA reductase in mammalian cells. The compounds are characterized by the formula

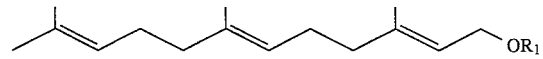

where $R_1$ may be a lower alkyl, or an acyl group

where $R_2$ may be any lower alkyl, wherein lower alkyl is of from 1 to 6 carbon atoms, particularly 1 to 4 carbon atoms, more particularly methyl, ethyl and propyl. The farnesyl compounds, particularly farnesyl acetate and farnesyl ethyl ether, decrease steady state levels of HMG CoA reductase, and block cholesterol synthesis.

The compounds are added to a host in a physiologically acceptable carrier, at a dosage from 5 mg to 1400 mg, more usually from 100 mg to 1000 mg, preferably 500 to 700 for a dose of 0.5 to 20 mg/kg weight. The dosage is elected so that the cholesterol biosynthesis is reduced by 40 to 80% and specifically the activity of HMG CoA reductase is reduced by about 20 to 80%, usually 40 to 50%.

Hypercholesterolemia patients are treated with a therapy comprising said farnesyl compounds, for the most part, farnesyl acetate or farnesyl ethyl ether. The compounds may be administered in a variety of ways, orally, parenterally, etc.

For injection, the farnesyl acetate or farnesyl ethyl ether may be injected subcutaneously, intraperitoneally, intravascularly, etc. Depending upon the manner of introduction, the compounds may be formulated in a variety of ways. The concentration of therapeutically active compound in the formulation may vary from about 0.5–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

For oral application, the pharmaceutical composition will generally contain from about 5–100% by weight of the active material. For other applications, the composition will generally have from about 0.5–50 wt. % of the active material. Various carries include excipients, sugars, alum, dimethyl sulfoxide, etc.

The subject compositions will generally be administered daily, in an amount to provide at least about a 20 to 50% decrease in the level of serum cholesterol. Generally, the total daily dosage will be at least about 10 mg, usually at least about 400 mg to 500 mg, preferably about 700 mg, and not more than about 1500 mg, usually not more than about 1000 mg. The amount may vary with the general health of the patient, the response of the patient to the drug, whether the farnesyl compound is used by itself or in combination with other drugs, and the like. Daily administrations may be one or more times, usually not more than about four times, particularly depending upon the level of drug which is administered.

Other cholesterol lowering agents, such as those which inhibit another enzyme in the biosynthetic pathway of cholesterol synthesis, may be used in combination with the subject compounds. Examples of such agents include but are not limited to HMG-CoA reductase inhibitors, HMG-CoA synthase inhibitors, squalene synthase inhibitors, and squalene epoxidase inhibitors. Specific compounds of interest include lovastatin, simvastatin, pravastatin and fluvastatin. Other cholesterol lowering compounds include niacin, probucol, fibric acids, clofibrate, gemfibrozol and LDL-receptor gene inducers, and zaragozic acid. The additional drugs may be administered separately or in conjunction with the farnesyl compounds and may be formulated in the same formulation. Representative of such combinations are those containing about 500–1500 mg of a farnesyl compound in combination with about 20–100 mg of an HMG-CoA reductase inhibitor or 250–1000 mg of probucol or 600–1200 mg of gemfibrozil or 1–2 g of clofibrate or 3–6 g of niacin, or 20–300 mg of an LDL-receptor gene inducer.

The following examples are offered by way of illustration and not by way of limitation.

EXPERIMENTAL

EXAMPLE I

Materials—All materials unless otherwise specified were readily available from commercial sources. [$^3$H]Acetic acid was purchased from New England Nuclear. Compactin was the generous gift of Dr. Akira Endo of Tokyo Noko University, Tokyo. Ethyl farnesyl ether was the generous gift of Dr. Christopher J. Silva of Stanford University. Farnesol, farnesyl acetate, geraniol, geranyl acetate, and 3-methyl-2-buten-1-ol were purchased from Aldrich Chemical Co. Farnesyl pyrophosphate and [1-$^3$H] farnesyl pyrophosphate were purchased from American Radiolabeled Chemicals of St. Louis, Mo. Tran$^{35}$S-label(>1,000 Ci/mmol) was purchased from ICN Biomedical Inc. Zaragozic acid A was the generous gift of Dr. James Bergstrom of Merck, Sharp & Dohme Research Laboratories.

Cell Culture—All cells were grown as monolayers at 37° C. in an atmosphere of 5% $CO_2$. CHO-HMGal cells were grown in minimal essential medium (MEM) supplemented with 0.25 mg/ml active geneticin and either 5% fetal calf serum (FCS) or 5% lipid-poor fetal calf serum (LPS).

Stock Solutions—Stock solutions of farnesyl acetate, ethyl farnesyl ether, and the mixture of 25-hydroxycholesterol with cholesterol were all made in 100% ethanol at 100 times the final concentration. In all experiments in which these compounds were used, there is a final concentration of 1% ethanol in the medium. For control, cells grown with "no additives" or "mevalonate" 100% ethanol was added to the medium to bring the final concentration of ethanol to 1%. The mevalonate stock solution was prepared at a concentration of 2M in 20 mM potassium phosphate buffer (pH 4.5).

β-galactosidase Specific Activity—In vitro β-galactosidase activity was measured using the substrate, o-nitrophenyl-β-D-galactopyranoside. Specific activities were calculated using protein concentration values.

Measurement of HMGal and HMG-CoA Reductase Synthesis Rates Cells plated into 60×15 mm dishes were grown in 5% LPS MEM with 0.25 mg/ml active geneticin for 24 hours. These cells were washed with PBS and grown for 24 hours in 5% LPS MEM supplemented with 0.25 mg/ml active geneticin, 10 μM compactin and 0.1 mM mevalonate. Either 20 mM mevalonate or 10 μg/ml farnesyl acetate was added to some of the plates as indicated in the figure legend. After 24 hours, the medium was removed, the cells were washed with PBS and the medium was replaced with methionine-free MEM supplemented with 5% LPS, 250 μg/ml of active geneticin, 10 μM compactin, and 0.1 mM mevalonate. In addition, 20 mM mevalonate or 10 μg/ml farnesyl acetate was included in those plates previously treated with these compounds. After 1 hour, the starvation medium was removed and replaced in each case with a medium of the same composition except that it included 75 μCi of Tran$^{35}$S-label (>1,000 Ci/mmol) and 30 μM cold methionine. Cells were harvested immediately and at 10 minute intervals up to 40 minutes. Cells were washed, lysed and the HMGal and HMG-CoA reductase proteins were immunoprecipitated, subjected to SDS-PAGE and quantified. In each case, two 50 μl aliquots of the cell lysates were used to determine the protein concentration, and two 25 μl aliquots were used to determine the amount of Tran$^{35}$S-label incorporated into total cellular protein by trichloroacetic acid precipitation method.

Measurement of HMGal and HMG-CoA Reductase Degradation Rates Cells grown in 60×15 mm dishes were washed once with ice-cold PBS and starved for 1 hour in 1 ml of methionine-free MEM supplemented with 5% LPS, 250 μg/ml of active geneticin, 10 μM compactin, and 0.1 mM mevalonate. These cells were radio-labeled for 2 hours in 300 μl of the methionine-free starvation medium containing 100 μCi of Tran$^{35}$S-label (>1,000 Ci/mmol). Cells were incubated in an MEM-based chase medium containing 2 mM methionine, 5% LPS, 250 μg/ml of active geneticin, 10

μM compactin, and 0.1 mM mevalonate. During the chase period, some plates also had either 20 mM mevalonate, 10 μg/ml farnesyl acetate or 10 μg/ml ethyl farnesyl ether added to them as indicated in the figure legend. Following the chase, cells were washed, lysed and the HMGal and HMG-CoA reductase proteins were immunoprecipitated, subjected to SDS-PAGE and quantified.

Lipid Saponification and Extraction Procedure Saponification and extraction of lipids from cell and media samples was performed as previously described in Bradfute, et al. (1992) J.B.C. 267:18308–18314.

Thin Layer Chromatography—TLC was performed using Analtech 250 μm silica gel G plates with a hexanes/diethyl ether (1:1) solvent system. Lipid standards were visualized by iodine staining. Bands were scraped from the plate and their radioactivity was measured.

Quantification of Radioactivity—Samples were suspended in 4 ml of scintillation fluid (Cytoscint from ICN). The radioactivity of the samples was measured using a Beckman LS-7500 scintillation counter.

Squalene Synthase Assay—The cell lysate was prepared immediately prior to running the assay. Cells were washed three times with PBS, once with a 0.1M potassium phosphate buffer (pH 7.4) containing 5 mM $MgCl_2$ and 5 mM CHAPS, and once with a 0.01M potassium phosphate buffer (pH 7.4) containing 0.5 mM $MgCl_2$ and 0.5 mM CHAPS. Cells were scraped with a rubber policeman in approximately 0.5 ml of the final wash buffer and dounce homogenized with 20 strokes, while on ice. An aliquot of cell lysate was examined with a light microscope to ensure that essentially all cells in the sample were lysed. An additional aliquot of cell lysate was saved for protein determination. The squalene synthase assay was performed under conditions in which tile substrate concentration was saturating and activity was linear with respect to protein concentration and time. The assay was performed under conditions previously described by Shechter, et al. (1992) J.B.C. 267:8628–8635, with a number of minor modifications. The concentration of farnesyl pyrophosphate was changed to 6.25 μM (1.6 Ci/mmol [$1-^3H$]farnesyl pyrophosphate). Samples were incubated for 30 minutes. The reaction was stopped by the addition of 20 μl of 0.5M EDTA (pH 8.0). After stopping the reaction, each sample received 5 μl of 10 mg/ml butylated hydroxytoluene as an antioxidant and 15 μl of 1% unlabeled squalene as a carrier. The entire reaction mixture was applied to a TLC plate in 20 μl aliquots which were allowed to dry before additional aliquots were applied to the same location. The squalene was isolated by TLC and the radioactivity of the squalene bands was measured as previously described. In calculating the specific activity, values were corrected for the replacement of one in four of the tritium atoms from the [$1-^3H$]farnesyl pyrophosphate by hydrogen from NADPH during the formation of squalene.

Results

Farnesyl acetate and ethyl farnesyl ether stimulate a reduction in HMGal activity—In an attempt to identify tile non-sterol metabolite(s) that triggers the down regulation of HMG-CoA reductase, five commercially available isoprenoid compounds were tested for their effects on HMGal activity in CHO-HMGal cells. Each of tile compounds tested closely resembled one of tile naturally occurring isoprenoid pyrophosphates, except that the pyrophosphate group had been replaced by either a hydroxyl or an ethyl ester group. The compounds tested included: 3-methyl-2-buten-1-ol, the alcohol of the five carbon isoprenoid-dimethylallyl pyrophosphate (a naturally occurring isomer of isopentenyl pyrophosphate); geraniol and geranyl acetate, the alcohol and the ethyl ester of the ten carbon isoprenoid-geranyl pyrophosphate; and farnesol and farnesyl acetate, the alcohol and the ethyl ester of the fifteen carbon isoprenoid-farnesyl pyrophosphate. Of the five isoprenoid compounds tested, only farnesyl acetate stimulated a reduction in HMGal activity at concentrations below the levels that were toxic to the CHO-HMGal cells.

To confirm that the reduction in HMGal activity was the result of a regulatory function specifically targeting the membrane domain of HMGal, the effects of farnesyl acetate on β-galactosidase activity were measured in vitro for both CHO-HMGal cells and CHO-Gal cells. The CHO-Gal cells had been stably transfected with a construct identical to the HMGal construct (using the same vector, promoter, and 5' and 3' flanking regions) except that the construct in the CHO-Gal cells codes for a soluble β-galactosidase protein instead of the HMGal fusion protein with the membrane domain of HMG-CoA reductase. In this experiment, the CHO-Gal cells served to control for any artifacts farnesyl acetate might cause in the β-galactosidase assay or any nonspecific effects farnesyl acetate might have on the rates of protein synthesis or degradation.

A 24 hour treatment with 10 μg/ml farnesyl acetate reduced HMGal activity in CHO-HMGal cells by 70%, while the β-galactosidase activity of CHO-Gal cells were not changed significantly. At the higher concentration of 20 μg/ml, the HMGal activity of CHO-HMGal cells was reduced by 80%, while the μ-galactosidase activity of CHO-Gal cells was essentially unchanged.

In addition to farnesyl acetate, the effects of ethyl farnesyl ether on β-galactosidase activity were measured in vitro for both CHO-HMGal cells and CHO-Gal cells. The structure of ethyl farnesyl ether is identical to that of farnesyl acetate except that the ethyl group is attached by an ether linkage to the farnesyl group instead of an ester linkage. While an esterase in CHO cells could possibly cleave the ethyl group from farnesyl acetate, the ether linkage would be stable. It seemed possible that ethyl farnesyl ether might remain active longer than farnesyl acetate and could not be metabolized to other potential regulatory molecules.

However, in most cases ethyl farnesyl ether proved to be less effective than farnesyl acetate, perhaps because of its toxicity. After treatment with 10 μg/ml ethyl farnesyl ether, the HMGal activity of CHO-HMGal cells was reduced by 40%, while the reduction of β-galactosidase activity in CHO-Gal cells was insignificant. At the higher concentration of 20 μg/ml, the specific effect that ethyl farnesyl ether exhibited on the membrane domain of HMGal was increased only slightly. The HMGal activity of CHO-HMGal cells was reduced by 50%, while the β-galactosidase activity of CHO-Gal cells was essentially unchanged.

Cell growth in farnesyl acetate and ethyl farnesyl ether CHO-HMGal cells were grown in a range of farnesyl acetate and ethyl farnesyl ether concentrations, in order to determine the optimal concentration of the farnesyl compounds to use in subsequent experiments. Cells grown in 10 μg/ml farnesyl acetate exhibit only a slight reduction in the rate o[cell growth over an 8 day period. Cells grown in 20 and 30 μg/ml exhibited a roughly 30% reduction in cell growth, while concentrations of 40 and 50 μg/ml result in substantial cell death. In the case of 50 μg/ml farnesyl acetate, essentially all cells were dead by the fourth day.

Ethyl farnesyl ether causes a greater retardation of cell growth and more cytotoxic effects at lower concentrations. Like farnesyl acetate, cells grown in 10 μg/ml ethyl farnesyl ether exhibit only a slight reduction in cell growth over an 8 day period. However, at 20 μg/ml, ethyl farnesyl ether reduces cell growth by approximately 60%. In addition, 20 µg/ml ethyl farnesyl ether induced cell death after 4 days, while substantial cell death was not observed in farnesyl acetate treated cells until concentrations reached 40 µg/ml. At ethyl farnesyl ether concentrations of 30 µg/ml and higher, essentially all cells were dead by the second day of treatment.

Farnesyl compounds reduce translation and stimulate degradation of HMG-CoA reductase and HMGal A reduction in HMGal specific activity triggered by the farnesyl compounds could have been the result of a decrease in HMGal synthesis, an increase in HMGal degradation, or a combination of changes in both the synthesis and degradation rates. In order to test whether the farnesyl compounds impact synthesis, the rates of HMGal, HMG-CoA reductase, and total cellular protein synthesis were measured by [$^{35}$S] methionine incorporation in the presence and absence of 10 µg/ml farnesyl acetate.

Neither farnesyl acetate nor mevalonate have a significant effect on total protein synthesis as measured by TCA-precipitable counts. However, farnesyl acetate triggers a 60% reduction in the rate of HMG-CoA reductase synthesis and a 80% reduction in the rate of HMGal synthesis. Similarly, mevalonate triggers a 70% reduction in HMG-CoA reductase synthesis and a 70% reduction in the rate of HMGal synthesis. Both mevalonate and farnesyl acetate reduce HMG-CoA reductase and HMGal synthesis by between 60 and 80%, while neither compound significantly alters total protein synthesis.

In order to test whether the farnesyl compounds impact degradation, the rates of degradation for HMGal, HMG-CoA reductase, and total cellular protein were measured in the presence and absence of 10 µg/ml farnesyl acetate and ethyl farnesyl ether. Neither farnesyl compound had a significant effect on the degradation of total cellular protein.

Previous studies have shown that the addition of 20 mM mevalonate can stimulate a 40% decrease in the half-lives of HMG-CoA reductase and HMGal. In this study, farnesyl acetate reduced the half-life of HMG-CoA reductase by 60% from 9.3 to 3.6 hours and reduced the half-life of HMGal by 40% from 6.4 to 3.9 hours. Ethyl farnesyl ether triggered an even greater increase degradation rates, reducing the half-life of HMG-CoA reductase by 70% from 9.3 to 2.9 hours and reducing the half-life of HMGal by 50% from 6.4 to 3.0 hours. Farnesyl acetate and ethyl farnesyl ether are at least as effective at stimulating the degradation of HMGal and HMG-CoA reductase as the addition of exogenous mevalonate.

Farnesyl acetate and ethyl .farnesyl ether directly inhibit cholesterol biosynthesis After establishing that the farnesyl compounds reduce the synthesis and increase the degradation of HMG-CoA reductase, we attempted to quantify the effect that these changes would have on cholesterol biosynthesis. To allow the cells to reach steady-state levels of HMG-CoA reductase in the presence of the farnesol or sterol compounds, CHO-HMGal cells were incubated for 24 hours with either farnesyl acetate, ethyl farnesyl ether, a mixture of 25-hydroxycholesterol and cholesterol, or no additives. Subsequently, the cells were labeled for 1,2, and 4 hours with [$^3$H]acetate and harvested. The non-saponifiable lipid fraction from each cell type was extracted and separated by TLC. The radioactivity that co-migrated with cholesterol was measured and normalized for the amount of cellular protein. For cells treated with a mixture of 25-hydroxycholesterol and cholesterol, there was 98% less radioactive material co-migrating with cholesterol than the cells that were incubated with no additives. Previous studies have demonstrated that exogenous sterols are able to reduce 95% of cholesterol biosynthesis by down regulating enzymes in the isoprenoid metabolic pathway, primarily HMG-CoA reductase. In this study, cells treated with the farnesyl compounds exhibited a substantial reduction in the incorporation of [$^3$H]acetate into cholesterol as well. Cells treated with farnesyl acetate for 24 hours showed a 80% reduction in [$^3$H]acetate incorporation into cholesterol, while cells treated with ethyl farnesyl ether for 24 hours showed a 95% reduction.

Farnesyl acetate and ethyl farnesyl ether could have reduced incorporation by down regulating HMG-CoA reductase, as 25-hydroxycholesterol does, or by directly inhibiting the enzymes that synthesize cholesterol. In a number of previous studies, some of the farnesyl compounds tested have demonstrated a potent competitive inhibition of squalene synthase, the enzyme that catalyzes the first committed step in sterol branch of the isoprenoid biosynthetic pathway. In addition, one study found that some of the farnesyl compounds tested function as general inhibitors of microsomal enzymes.

To determine if tile drop in cholesterol incorporation, which was stimulated by the farnesyl compounds, resulted from tile inhibition of cholesterol biosynthetic enzymes, the [$^3$H]acetate incorporation experiment was repeated without pretreating the cells for 24 hours with the farnesyl compounds. Farnesyl acetate and ethyl farnesyl ether were only present during the labeling period so that any reduction in incorporation into cholesterol would be the result of inhibition and not a down regulation in HMG-CoA reductase. Cells treated with farnesyl acetate only during the labeling period showed an 89% reduction in incorporation into cholesterol, while cells treated with ethyl farnesyl ether only during the labeling period showed a 98% reduction. These reductions in cholesterol synthesis demonstrate that the farnesyl compounds directly inhibit a cholesterol biosynthetic enzyme(s).

Since both farnesyl compounds have a structural similarity to farnesyl pyrophosphate, the substrate for squalene synthase, and some of the farnesyl compounds that have been tested function as a competitive inhibitor of squalene synthase, the effects of farnesyl acetate on in vitro squalene synthase activity was measured. As a positive control, squalene synthase activity was also measured in tile presence of zaragozic acid A, a potent competitive inhibitor of the enzyme. At concentrations ranging from 4 nM to 0.2 mM, farnesyl acetate had a negligible effect on squalene synthase activity. The concentration of farnesyl acetate used in the rest of this study, 10 µg/ml (37.8 µM) was less than 20% of the highest concentration tested, a concentration which showed no significant effect on squalene synthase activity. At concentrations ranging from 1 nM to 50 µM, zaragozic acid A inhibited in vitro squalene synthase activity by more than 90%.

To determine tile site of tile metabolic block caused by farnesyl acetate and ethyl farnesyl ether, the non-saponifiable lipids from cells grown in the presence of the farnesyl compounds were examined for the accumulation of intermediates in the cholesterol biosynthetic pathway. The cells were only labeled for 1 hour and only treated with the farnesyl compounds during the labeling period; so that any intermediates which accumulated would be as a result of the inhibitory effects of the farnesol compounds and not subsequent regulatory effects on HMG-CoA reductase. CHO-HMGal cells were incubated with [$^3$H]acetate and either farnesyl acetate, ethyl farnesyl ether, or no additive. The non-saponifiable lipids were isolated from both the cell, and the medium and separated by TLC.

The cells not treated with farnesyl or sterol compounds primarily utilized [³H]acetate to synthesize metabolites that co-migrated with cholesterol, and to a lesser extent lanosterol. Of the radioactivity in the cell-derived fraction of the untreated cells, 62% co-migrated with cholesterol, 24% co-migrated with lanosterol, and the remaining 14% was scattered fairly evenly throughout the rest of the TLC lane. In addition, almost all of the products derived from [³H] acetate remained in the cells. Of the total radioactivity in the non-saponifiable lipid fraction of the untreated cells, 94% was found in the cells and only 6% was found in the medium.

In contrast, the cells treated with farnesyl acetate primarily utilized [³H]acetate to synthesize compounds that co-migrate with lanosterol, and to a lesser extent squalene. Of the radioactivity in the cell-derived fraction of the farnesyl acetate treated cells, 74% co-migrated with lanosterol, 9% co-migrated with squalene, and only 4% co-migrated with cholesterol. The remaining 13% was scattered fairly evenly throughout the rest of the TLC lane. While the amount of media-derived material that co-migrated with farnesol increased almost 3 fold in the farnesyl acetate treated sample, it still accounts for a relatively small proportion of the total non-saponifiable material synthesized. Of the total radioactivity from both non-saponifiable lipid fractions, 88% was found in the cells, while 12% was found in the medium, up from 6% in the untreated sample.

Like the cells treated with farnesyl acetate, ethyl farnesyl ether treated cells synthesized very little cholesterol and accumulated more compounds that co-migrated with lanosterol, squalene, and to a lesser extent farnesol. However, in the case of ethyl farnesyl ether, much more squalene was accumulated. Of the radioactivity in the cell-derived fraction of the ethyl farnesyl ether treated cells, 48% co-migrated with lanosterol, 45% co-migrated with squalene, and only 1% co-migrated with cholesterol. The remaining 6% was scattered fairly evenly throughout the rest of the TLC lane. The addition of ethyl farnesyl ether cause a 2 fold increase in the amount of media-derived material that co-migrated with farnesol, but the media derived counts remained a small portion of the total counts. Of the total radioactivity from both non-saponifiable lipid fractions in the ethyl farnesyl other sample, 86% was found in the cells, while 14% was found in the medium, tip from 6% in the untreated sample.

It is evident from these results that farnesyl acetate and farnesyl ethyl ether are effective in stimulating post-transcriptional down-regulation of HMG-CoA reductase, the rate limiting enzyme in the synthesis of cholesterols and isoprenoids.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for treating a patient for hypercholesterolemia, said method comprising:

administering to said patient an amount effective to reduce the level of serum cholesterol, of a compound of the formula:

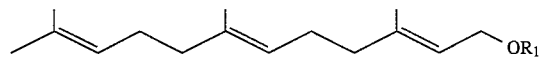

where $R_1$ is a lower alkyl of from 1 to 4 carbon atoms, or an acyl group

where $R_2$ is a lower alkyl of from 1 to 4 carbon atoms.

2. A method according to claim 1, wherein said compound is farnesyl ethyl ether.

3. A method according to claim 1, wherein said compound is farnesyl acetate.

4. A method according to claim 1, wherein said amount is effective to reduce the level of serum cholesterol from about 20 to 50%.

* * * * *